United States Patent [19]
Felardos et al.

[11] Patent Number: 5,866,111
[45] Date of Patent: Feb. 2, 1999

[54] COSMETIC COMPOSITION INCLUDING A FILM-FORMING POLYMER AND SUGAR ESTERS

[75] Inventors: Christian Felardos, Chevilly Larue; Christine Aygat-Cano, Fargeau Ponthierry; Nathalie Collin, Sceaux, all of France

[73] Assignee: L'Oreal, Paris, France

[21] Appl. No.: 810,342

[22] Filed: Feb. 27, 1997

[30] Foreign Application Priority Data

Feb. 29, 1996 [FR] France ................................ 96-02561

[51] Int. Cl.⁶ ........................................................ A61K 7/06
[52] U.S. Cl. ..................................... 424/70.22; 424/70.24; 424/70.31; 424/70.6; 424/70.7
[58] Field of Search ................................ 424/401, 70.22, 424/70.23, 70.24, 70.31, 70.6, 70.7; 514/53, 777

[56] References Cited

U.S. PATENT DOCUMENTS 5,534,247  7/1996  Franjac et al. ........................ 424/707

FOREIGN PATENT DOCUMENTS 042157    12/1981  European Pat. Off. .
647443     4/1995  European Pat. Off. .
WO 94/17775 8/1994  WIPO .

*Primary Examiner*—Nathan M. Nutter
*Attorney, Agent, or Firm*—Finnegan, Henderson, Farabow, Garrett & Dunner, L.L.P.

[57] ABSTRACT

The invention relates to new cosmetic compositions, in particular mascaras, based on at least one film-forming polyester polymer and sugar esters. These mascaras have properties of eyelash elongation, of eyelash curving, of adhesion to the eyelash and of tolerance by the eyelash which are improved in comparison with the mascaras existing on the market.

28 Claims, No Drawings

COSMETIC COMPOSITION INCLUDING A FILM-FORMING POLYMER AND SUGAR ESTERS

The invention relates to new cosmetic compositions, in particular mascara compositions, that have high-performance make-up properties combined with very great softness. The invention relates more particularly to new mascara compositions based on at least one film-forming polymer and sugar esters.

Numerous mascara formulations exist on the market; however, the consumer always expects an improvement in the properties of these mascaras, be it the lengthening of the eyelash, the curving of the eyelash, better adhesion of the composition to the eyelash or better tolerance by the eyelash.

Mascara compositions including a water-dispersible polyester polymer are known from U.S. Pat. No. 5,389,363, the disclosure of which is herein incorporated by reference, this mascara possessing good adhesiveness and eyelash elongation properties. However, this property of elongation is obtained only by the combined effect of this polyester and of another, oil-soluble synthetic polymer, the two polymers being introduced respectively in a gel and in an oil-in-water emulsion, the two phases being prepared extemporaneously and then mixed to give the mascara composition. The composition and the process for the preparation of this mascara have the disadvantage of being complex.

Furthermore, according to document U.S. Pat. No. 5,053,221, the disclosure of which is incorporated by reference, there are known mascara compositions including a water-dispersible polyester polymer which does not flake and is light, soft and lengthening for the eyelashes and the make-up of which can be removed with water. These compositions have the particular feature of not including waxes. On the other hand, they include microspherical particles which contribute to the speed of drying. These compositions may additionally include, as emulsifiers, methylglucose sesquistearate and methyl gluceth-20 sesquistearate. These mascara compositions, which do not include waxes, have the disadvantage of giving a make-up which is too natural, not very lengthening, not very curving and which does not adhere well to the eyelash.

Furthermore, a person skilled in the art is aware of the very good tolerance, by the skin and by hair, of sugar esters when they are employed as emulsifiers. However, if a composition is prepared from conventional ingredients of mascara compositions (waxes, pigments, gelling agents, traditional film-formers like hydroxyethyl cellulose, drying agents like silica) and including a water-dispersible film-forming polyester polymer and glucose esters of fatty acids, polyoxyethylenated or otherwise, then fairly disappointing results are obtained which do not make it possible to forecast any special advantage of this category of products in mascara compositions.

Consequently, it is with surprise and astonishment that the inventors have discovered new mascara compositions based on at least one film-forming polymer and sugar esters which, when compared with the compositions of the prior art, permit better lengthening and better curving of the eyelash and better adhesion of the composition to the eyelash, which are combined with very good tolerance by the eyelash and by the eye.

The compositions according to the invention are characterized in that they include:
- at least one wax,
- at least one anionic film-forming polymer of polyester type, and
- at least one ester of fatty acid and of sucrose.

Preferably, the compositions according to the invention include, by weight in relation to the total weight of the composition:

from 5 to 30% of at least one wax,
from 0.1 to 25% of at least one anionic film-forming polymer of polyester type, and
from 0.5 to 20% of at least one ester of fatty acid and of sucrose.

In the present description the percentages of products in the compositions according to the invention are given as mass in relation to the total mass of the composition. The mass of polymer in the composition is counted as dry solids.

The use of sugar esters according to the invention makes it possible to obtain a composition whose consistency allows easy application and good adhesion of the mascara. The formulations are very well tolerated, even by the users who have sensitive eyes, given that the sugar esters employed are nonionic and therefore have an improved harmlessness. In addition, after the removal of make-up from the eyelashes, the latter retain an appearance of softness and suppleness. In addition, the use of sugar esters according to the invention makes it possible to stabilize the emulsions, especially the wax-in-water emulsions, not including any emulsifier other than the esters.

According to a preferred embodiment of the invention, the degree of esterification of the sucrose in the ester of fatty acid and of sucrose is greater than or equal to two.

The ester of fatty acid and of sucrose is preferably selected from the products corresponding to the formula (I):

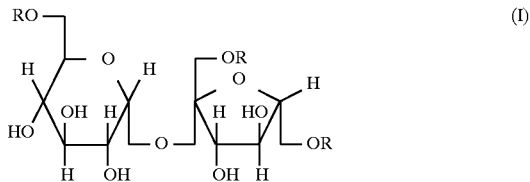

in which the substituents R, which are identical or different, denote a proton or a group:

with R' denoting a $C_{12}$–$C_{22}$ saturated or unsaturated, linear or branched alkyl group, at least one of the substituents R being other than a proton. R' is preferably selected from $C_{16}$–$C_{18}$ saturated or unsaturated, linear or branched alkyl groups.

According to a preferred embodiment of the invention, the compositions according to the invention additionally include at least one ester of monosaccharide and/or alkyl monosaccharide. This monosaccharide may be selected, for example, from pentoses, among which there may be mentioned D-ribose, D-arabinose, D-xylose, D-lyxose, D-ribulose, D-xylulose, hexoses such as, for example, D-allose, D-altrose, D-glucose, D-mannose, D-gulose, D-idose, D-galactose, D-talose, D-fructose, D-sorbose and D-tagatose, and heptoses such as D-mannoheptulose and D-sedoheptulose.

The monosaccharide is preferably an alkylglucose.

The compositions according to the invention preferably additionally include up to 15% by weight of at least one alkylglucose ester.

According to a preferred embodiment of the invention, the alkylglucose ester is selected from the polyoxyethylenated fatty esters of ($C_1$–$C_6$-alkyl)glucose.

The alkylglucose ester is preferably selected from the products corresponding to the formula (II):

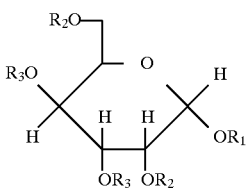

(II)

in which $R_1$ denotes a hydrogen atom or a $C_1$–$C_6$ saturated or unsaturated, linear or branched alkyl group, the groups $R_2$, which are identical or different, denote a proton or a group:

$R'_2$ denoting a $C_{12}$–$C_{22}$ saturated or unsaturated, linear or branched alkyl group, at least one of the groups $R_2$ being other than a proton, and the groups $R_3$, which are identical or different, denote a hydrogen atom or a —($CH_2$—$CH_2$O)$_n$—H group, at least one of the groups $R_3$ being other than a proton, with n ranging from 50 to 200.

The compositions according to the invention preferably include a mixture of sugar esters comprising from 30 to 100% of at least one sucrose ester according to formula (I) and from 0 to 70% of at least one glucose ester according to formula (II), by weight relative to the total weight of the sugar esters.

Still more preferably, the compositions according to the invention include a mixture of sugar esters comprising from 60 to 80% of at least one sucrose ester according to formula (I) and from 20 to 40% of at least one glucose ester according to formula (II). The quantity of sugar esters present in the composition according to the invention preferably ranges from 1 to 20% by weight of the composition.

The film-forming polymer employed within the scope of the invention is of polyester type and may additionally include sequences of amide, amine or urethane type and/or fatty chains. The film-forming polymer is preferably anionic and is dispersible in water. It may, however, be dissolved in the mixture.

The film-forming polymers that can be employed in the present invention are preferably chosen from water-dispersible anionic polyester and/or polyesteramide polymers including monomers carrying an —$SO_3M$ functional group, with M denoting a hydrogen atom, an ammonium ion $NH_4^+$ or a metal ion such as, for example, an $Na^+$, $Li^+$, $K^+$, $Mg^{2+}$, $Ca^{2+}$, $Cu^{2+}$, $Fe^{2+}$ or $Fe^{3+}$ ion. The polymers described in U.S. Pat. No. 3,734,874, U.S. Pat. No. 4,233,196 and U.S. Pat. No. 4,304,901, the disclosures of which are herein incorporated by reference, may be mentioned in particular.

Advantageously employed in the present invention are film-forming polyester polymers based on at least one dicarboxylic acid, at least one diol and at least one difunctional aromatic monomer additionally carrying an —$SO_3M$ group as described above.

The dicarboxylic acid preferably may be aliphatic, alicyclic or aromatic. Examples of such acids which may be mentioned are: oxalic acid, malonic acid, dimethylmalonic acid, succinic acid, glutaric acid, adipic acid, pimelic acid, 2,2-dimethylglutaric acid, azelaic acid, sebaric acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 4,4'-sulphonyldibenzoic acid, 2,5-naphthalenedicarboxylic acid and 2,6-naphthalenedicarboxylic acid. These dicarboxylic acid monomers may be employed by themselves or as combination of at least two dicarboxylic acid monomers. Among these monomers those preferably chosen are phthalic acid, isophthalic acid and terephthalic acid.

The diol may be selected from aliphatic, alicyclic and aromatic diols. The diol employed is preferably selected from ethylene glycol, diethylene glycol, triethylene glycol, 1,3-propanediol, cyclohexanedimethanol and 4-butanediol. The aromatic nucleus of the difunctional aromatic monomer additionally carrying an —$SO_3M$ group as described above may be selected, for example, from benzene, naphthalene, anthracene, diphenyl, oxydiphenyl, sulphonyldiphenyl and methylenediphenyl nuclei. Examples of difunctional aromatic monomers additionally carrying an —$SO_3M$ group which may be mentioned are sulphoisophthalic acid, sulphoterephthalic acid, sulphophthalic acid and 4-sulphonaphthalene-2,7-dicarboxylic acid. In the compositions that are the subject-matter of the invention, it is preferred to employ copolymers based on isophthalate/sulphoisophthalate, and more particularly copolymers obtained by condensation of diethylene glycol, cyclohexanedimethanol, isophthalic acid and sulphoisophthalic acid. Such polymers are sold, for example, under the trade name EASTMAN AQ by Eastman Chemical Products. It is also possible to employ in the compositions forming the subject-matter of the present invention the polymers marketed by Rhône-Poulenc under the trade name POLYCARE. Such polyester polymers may be employed by themselves or as mixtures.

The film-forming polymer is employed in quantities that make it possible to obtain good adhesion of the composition to the eyelash, a lengthening, a sheathing and a curving which give an impression of an open look, the eyelashes being well separated.

The compositions according to the invention preferably include a quantity of film-forming polymer ranging from 0.1 to 25% by weight relative to the total weight of the composition. The compositions that form the subject-matter of the present invention preferably include a quantity of film-forming polymer ranging from 1 to 10% by weight relative to the total weight of the composition.

The compositions according to the present invention preferably additionally include at least one coemulsifier preferably chosen from fatty alcohols, fatty acids and glycerol fatty esters. The fatty chains of the fatty alcohols, of the fatty acids and of the glycerol fatty esters are usually of a length ranging from 12 to 22 carbon atoms. Coemulsifiers that can be employed in the present invention which may be mentioned are stearyl alcohol, cetyl alcohol, glyceryl stearate and stearic acid. The coemulsifiers are introduced into the compositions according to the invention in quantities ranging from 0 to 10% on a mass basis relative to the total mass of the invention, and preferably from 1 to 4%.

The waxes may be chosen from animal and vegetable waxes like, for example, carnauba wax, candelilla wax, beeswax, whale wax, rice wax, microcrystalline waxes and lanolins; the waxes are advantageously present in the compositions forming the subject-matter of the invention in quantities ranging from 5 to 30%, preferably from 10 to 25% by weight.

The compositions according to the invention additionally include compounds that are well known to a person skilled in the art for the preparation of mascara compositions, and among which there may be mentioned more particularly (a) water, preferably in an amount ranging from 30 to 80%, (b) gelling agents such as, for example, hydroxyethyl cellulose, which are preferably employed in an amount ranging from 0 to 3%, (c) pigments such as, for example, metal oxides, preferably in an amount ranging from 0.5 to 20%, (d) emollients, preferably employed in an amount ranging from 1 to 10%, (e) preservatives such as, for example, imidazolinylurea, methylparaben and propylparaben; (f) volatile oils which will evaporate in contact with the eyelash, but the presence of which in the cosmetic composition is useful because they facilitate the spreading of the composition when being applied, (g) other fatty substances such as, for example, mixtures of gum or of silicone resin with a volatile oil, (h) fillers such as, for example, silica, kaolin, talc and silk powder, which are preferably employed in an amount ranging from 0 to 15%, and (i) nonionic hydrophilic film-forming polymers preferably in an amount ranging from 0 to 3% by weight.

The compositions according to the invention are preferably in the form of wax-in-water emulsions; they may also be in the form of aqueous dispersions, of oily dispersions, of water-in-oil emulsions, of oil-in-water emulsions, of water-in-wax emulsions and of gels.

The compositions according to the invention may find an application as a make-up product such as mascara, lip rouge, foundation, eyeliner, hair-styling or a hair-care product and/or skin-care product, such as a care cream or sun product.

The invention is illustrated in greater detail in the following examples.

EXAMPLES

In the compositions described below the compounds employed were:

a) as film-forming polymer:

copolymers obtained by condensation of diethylene glycol, cyclohexanedimethanol, isophthalic acid and sulphoisophthalic acid:
P1=EASTMAN AQ 55S,
P2=EASTMAN AQ 38S,
P3=EASTMAN AQ 48 ultrapolymer, which are marketed by Eastman, other anionic, sodium polymethacrylate:
P4=DARVAN 7 (marketed by Vanderbilt), other:
P5 =GANEX WP660 (marketed by ISP), polyvinylpyrrolidone/1-triacontene copolymer.

b) sucrose esters: table 1

TABLE I

| Sugar esters | | | |
|---|---|---|---|
| Designation | Chemical name | Trade name/ Supplier | Substitution |
| S1 | Sucrose monodipalmitostearate | GRILLOTEN P8E 141G/Grillo | |
| S2 | Oxyethylenated methylglucose dioleate (120 OE) | GLUCAMATE DOE-120/Amerchol | |
| S3 | Sucrose stearate | RYOTO SUGAR ESTER S770 Mitsubishi | Mono: 38%/ di: 34%/ tri: 23%/ tetra: 3%/ penta: 2% |
| S4 | Sucrose laurate | SISTERNA L70-C/Sisterna | 70% of monoester |

TABLE I-continued

| Sugar esters | | | |
|---|---|---|---|
| Designation | Chemical name | Trade name/ Supplier | Substitution |
| S5 | Methylglucose monodistearate and polyglycerine-3 stearate | TEGO-CARE 450/ Goldschmidt | |
| S6 | Methylglucose sesquiisostearate | GRILLOCOSE IS/Grillo | |

Examples 1 to 15

Mascara formulations were prepared by forming a homogeneous mixture from:

| | |
|---|---|
| mixture of animal and vegetable waxes | 13.5% |
| lack iron oxide | 7% |
| film-forming polymer | p% |
| sugar esters | s% |
| hydroxyethyl cellulose | 0.9% |
| silicone oil | 0.15% |
| silicone gum (molecular weight $10^5$) | 0.14% |
| cyclopentadimethylsiloxane | 0.86% |
| 98% stearyl alcohol | 2.25% |
| preservative | 0.7% |
| sterilized demineralized waters q.s. | 100% | by varying the nature and the quantity (p, s) of the film-forming polymer and of the sugar esters.

In Example 10, the polymer was replaced with water.

In Example 11, the sugar esters were replaced with a substitution mixture denoted MS and consisting of 7.25% of stearic acid and 3.75% of triethanolamine, by weight relative to the total weight of the composition.

The properties of the mascaras were given marks from 1 to 5 in accordance with the scale:

dispersion: 1=very well dispersed; 5=coarse dispersion, fluidity: 1=very fluid; 5=very thick, adhesiveness: 1=very good adhesiveness; 5=poorly adherent, sheathing: 1=very sheathing; 5=very poorly sheathing, drying: 1=very fast drying; 5=very slow drying, lengthening: 1=very lengthening; 5=very poorly lengthening, curvature: 1=very curving; 5=very poorly curving.

The viscosity was evaluated in Pa s.

The results of the tests carried out are summarized in Table II below.

The compositions of Examples 1 to 5, 8, 14–15 form part of the invention. The compositions of Examples 6–7 and 9–13 are comparative.

TABLE II

| Example | Polymer nature/p | Sugar ester nature/s | viscosity | pH | dispersion | fluidity | adhesiveness | sheathing | drying | lengthening | curvature | findings |
|---|---|---|---|---|---|---|---|---|---|---|---|---|
| 1 | P1/2% | S1/6% S2/2% | 10.6–11.3 | 7.5 | 1 | 3 | 1 | 2 | 2 | 2 | 2 | make-up smooth and fast |
| 2 | P2/2% | S1/6% S2/2% | 9.5–9.7 | 7.3 | 1 | 3 | 2 | 3 | 2 | 2 | 2 | good make-up result |
| 3 | P3/2% | S1/6% S2/2% | 8.5—8.5 | 7.25 | 1 | 2 | 2 | 2 | 2 | 2 | 2 | good make-up result |
| 4 | P1/2% | S3/8% | 4.7—4.7 | 5.8 | 2 | 1 | | | | | | not tested |
| 5 | P1/2% | S4/8% | 3.1—3.1 | 5.6 | 5 | 1 | | | | | | not tested |
| 6 | P1/2% | S5/8% | 10.6–11.8 | 6.2 | 2 | 3 | 2 | 2 | 4 | 3 | 3 | deposition not very homogeneous; long drying |
| 7 | P1/2% | S6/8% | too thick; set solid | | 5 | 5 | | | | | | impossible to use for make-up |
| 8 | P1/2% | S1/8% | 8.7–9.5 | 7.5 | 2 | 2 | 2 | 3 | 2 | 2 | 2 | mascara smooth and creamy |
| 9 | P1/2% | S2/8% | 1.4–1.5 | 5.65 | 5 | 1 | | | | | | pigment poorly dispersed; too acid; liquid |
| 10 | 0 | S1/6% S2/2% | 8.7–9.0 | 7.5 | 2 | 2 | 5 | 4 | 4 | 4 | 4 | make-up lengthy |
| 11 | P1/2% | M.S. | 9.5–10.9 | 8.35 | 4 | 3 | 3 | 3 | 3 | 3 | 3 | make-up granular, less smooth |
| 12 | P4/8% | S1/6% S2/2% | 4.5–5.0 | 7.6 | 2 | 1 | 4 | 4 | 3 | 4 | 4 | make-up too natural, lengthy to apply |
| 13 | P5/5% – P1/1% | S1/6% – S2/2% | 9.7–10.4 | 7.5 | 2 | 3 | 3 | 4 | 4 | 3 | 3 | mascara poorly loading; eyelashes poorly thickened |
| 14 | P1/5% | S1/6% + S2.2% | 13.9–15.1 | 7.23 | 2 | 4 | 1 | 2 | 1 | 2 | 2 | mascara dries very quickly |
| 15 | P1/7% | S1/6% + S2/2% | 20.1–22.4 | 7.61 | 2 | 4 | 1 | 2 | 1 | 2 | 2 | mascara dries very quickly |

Example 16

Mascara compositions were prepared according to a formulation which differed from that given in Example 1 in the absence of stearyl alcohol (0%) and optionally a larger quantity of hydroxyethyl cellulose (0.9 to 2%). The compositions obtained were in the form of very well dispersed fine emulsions that had a pH in the region of 7.5 and exhibited good adhesiveness to the eyelash. These compositions, which lengthened and curved the eyelash very well, gave a very satisfactory make-up.

Example 17

A mascara composition was prepared according to a formulation which differed from that given in Example 1 in the replacement of the sugar esters S1 and S2 with a mixture of 2% of methylglucose sesquistearate and 6% of oxyethylenated methylglucose sesquistearate, on a mass basis relative to the total mass of the composition. A formulation was obtained which had a pH of 5.75, too acidic for the eyes. It was therefore necessary for this formulation to be neutralized by the addition of 0.04% of sodium hydroxide. The emulsion obtained was not very fine, was very fluid and did not adhere well to the eyelash. In addition, it dried very slowly. The make-up obtained was too natural.

Example 18

A mascara composition was prepared according to a formulation which differed from that given in Example 1 in the replacement of the sugar esters S1 and S2 with 8% of nonoxyethylenated methylglucose dioleate. The composition obtained was too liquid to be employed as mascara.

We claim:

1. A cosmetic composition comprising:
   at least one wax,
   at least one anionic film-forming polyester polymer, and
   a mixture of sugar esters comprising at least one fatty acid ester of sucrose, and at least one ester of a monosaccharide and/or an alkyl monosaccharide.

2. A composition according to claim 1, wherein said composition comprises, by weight in relation to the total weight of the composition:
   from 5 to 30% of at least one wax,
   from 0.1 to 25% of at least one anionic film-forming polyester polymer, and
   from 0.5 to 20% of at least one fatty acid ester of sucrose.

3. A composition according to claim 1, wherein the degree of esterification of the sucrose in the fatty acid ester of sucrose is greater than or equal to two.

4. A composition according to claim 1, wherein said at least one fatty acid ester of sucrose is selected from the products corresponding to the formula (I):

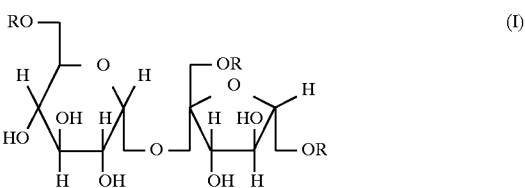

in which the substituents R, which are identical or different, each independently denotes a proton or a group:

wherein R' denotes a $C_{12}$–$C_{22}$ alkyl group, and wherein at least one of the substituents R is a moiety other than a proton.

5. A composition according to claim 1, wherein said ester of monosaccharide and/or alkyl monosaccharide is an alkylglucose ester.

6. A composition according to claim 5, wherein said alkylglucose ester is selected from polyoxyethylenated fatty esters of ($C_1$–$C_6$-alkyl)glucose.

7. A composition according to claim 5, wherein said alkylglucose ester is selected from compounds corresponding to the formula (II):

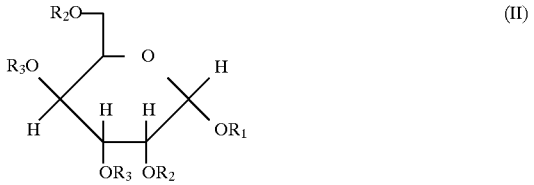
(II)

in which $R_1$ denotes a hydrogen atom or a $C_1$–$C_6$ alkyl group, the groups $R_2$, which are identical or different, each independently denote a proton or a group:

wherein $R'_2$ denotes a $C_{12}$–$C_{22}$ alkyl group, wherein at least one of the groups $R_2$ is a moiety other than a proton, and the groups $R_3$, which are identical or different, independently denote a hydrogen atom or a —($CH_2$—$CH_2O$)$_n$—H group, wherein at least one of the groups $R_3$ is a moiety other than a proton, and wherein n ranges from 50 to 200.

8. A composition according to claim 5, wherein said at least one alkylglucose ester is present in an amount up to 15% by weight, relative to the total weight of the composition.

9. A composition according to claim 1, wherein said at least one fatty acid ester of sucrose is present in said composition in an amount ranging from 30 to 80% by weight, relative to the total weight of the sugar esters, and is a sucrose ester according to formula (I):

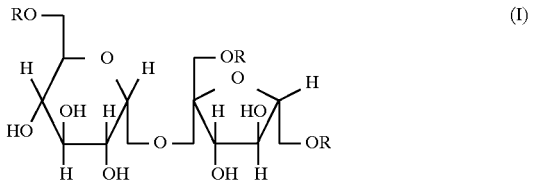
(I)

in which the substituents R, which are identical or different, each independently denotes a proton or a group:

wherein R' denotes a $C_{12}$–$C_{22}$ alkyl group, and wherein at least one of the substituents R is a moiety other than a proton, and wherein said ester of a monosaccharide and/or an alkyl monosaccharide is present in said composition in an amount ranging from 20 to 70% by weight, relative to the total weight of the sugar esters, and is a glucose ester according to formula (II):

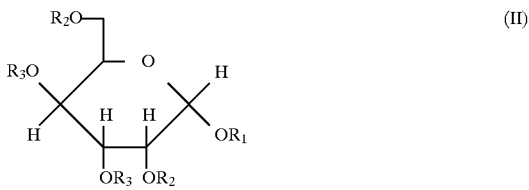
(II)

in which $R_1$ denotes a hydrogen atom or a $C_1$–$C_6$ alkyl group, the groups $R_2$, which are identical or different, each independently denote a proton or a group:

wherein $R'_2$ denotes a $C_{12}$–$C_{22}$ alkyl group, wherein at least one of the groups $R_2$ is a moiety other than a proton, and the groups $R_3$, which are identical or different, independently denote a hydrogen atom or a —($CH_2$—$CH_2O$)$_n$—H group, wherein at least one of the groups $R_3$ is a moiety other than a proton, and wherein n ranges from 50 to 200.

10. A composition according to claim 9, wherein said mixture of sugar esters comprises from 60 to 80% of said at least one sucrose ester according to formula (I) and from 20 to 40% of said at least one glucose ester according to formula (II).

11. A composition according to claim 1, wherein said at least one anionic film-forming polyester polymer comprises at least one sequence selected from amine, amide and urethane sequences and fatty chains.

12. A composition according to claim 1, wherein said at least one anionic film-forming polyester polymer is dispersible in water.

13. A composition according to claim 1, wherein said at least one anionic film-forming polyester polymer is selected from water-dispersible anionic polyester and polyesteramide polymers having monomers carrying an —$SO_3M$ functional group, wherein M denotes a hydrogen atom, an ammonium ion $NH_4^+$ or a metal ion.

14. A composition according to claim 1, wherein said at least one anionic film-forming polyester polymer is based on at least one dicarboxylic acid, at least one diol, and at least one difunctional aromatic monomer additionally carrying an —$SO_3M$ group;

wherein M represents a hydrogen atom, an ammonium ion, or a metal ion.

15. A composition according to claim 14, wherein said at least one dicarboxylic acid is selected from phthalic acid, isophthalic acid and terephthalic acid.

16. A composition according to claim 14, wherein said at least one diol is selected from ethylene glycol, diethylene glycol, triethylene glycol, 1,3-propanediol, cyclohexanedimethanol and 4-butanediol.

17. A composition according to claim 14, wherein said at least one difunctional aromatic monomer additionally carrying an —$SO_3M$ group is selected from sulphoisophthalic acid, sulphoterephthalic acid, sulphophthalic acid and 4-sulphonaphthalene-2,7-dicarboxylic acid.

18. A composition according to claim 1, wherein said at least one anionic film-forming polyester polymer is based on isophthalate/sulphoisophthalate.

19. A composition according to claim 1, wherein said at least one anionic film-forming polyester polymer is present in said composition in an amount ranging from 0.1 to 25% by weight relative to the total weight of the composition.

20. A composition according to claim 19, wherein said at least one anionic film-forming polyester polymer is present in said composition in an amount ranging from 1 to 10% by weight relative to the total weight of the composition.

21. A composition according to claim 1, wherein said composition further comprises at least one coemulsifier.

22. A composition according to claim 21, wherein said at least one coemulsifier is selected from fatty alcohols, fatty acids and glycerol fatty esters.

23. A composition according to claim 1, wherein said at least one wax is present in said composition in an amount ranging from 5 to 30% by weight relative to the total weight of the composition.

24. A composition according to claim 1, wherein said composition is in the form of a wax-in-water emulsion, an aqueous dispersion, an oily dispersion, a water-in-oil emulsion, an oil-in-water emulsion, a water-in-wax emulsion or a gel.

25. A composition according to claim 1, wherein said composition is in the form of a make-up product, a hair-styling or hair-care product, or a skin care product.

26. A composition according to claim 25, wherein said composition in the form of a make-up product is mascara, lip rouge, foundation, or eyeliner.

27. A composition according to claim 25, wherein said composition in the form of a skin care product is a care cream or a sun product.

28. The cosmetic composition according to claim 1, wherein said mixture of sugar esters is present in said composition in an amount ranging from 1 to 20% by weight of the total composition.

* * * * *